(12) United States Patent
McCarty et al.

(10) Patent No.: US 11,020,379 B2
(45) Date of Patent: Jun. 1, 2021

(54) 3-(PHENYL)-N-(4-PHENOXYBENZYL)-1,2,4-OXADIAZOLE-5-CARBOXAMIDE COMPOUNDS FOR THE MANAGEMENT OF CFTR PROTEIN MEDIATED DISEASES

(71) Applicants: Emory University, Atlanta, GA (US); Children's Healthcare of Atlanta, Inc., Atlanta, GA (US)

(72) Inventors: Nael McCarty, Atlanta, GA (US); Guiying Cui, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 16/697,188

(22) Filed: Nov. 27, 2019

(65) Prior Publication Data

US 2020/0085796 A1 Mar. 19, 2020

Related U.S. Application Data

(62) Division of application No. 15/578,159, filed as application No. PCT/US2016/034682 on May 27, 2016, now Pat. No. 10,512,636.

(60) Provisional application No. 62/167,999, filed on May 29, 2015.

(51) Int. Cl.
| | |
|---|---|
| *A61K 31/4245* | (2006.01) |
| *A61K 31/443* | (2006.01) |
| *A61P 11/06* | (2006.01) |
| *A61P 11/00* | (2006.01) |
| *A61K 47/36* | (2006.01) |

(52) U.S. Cl.
CPC ........ *A61K 31/4245* (2013.01); *A61K 31/443* (2013.01); *A61K 47/36* (2013.01); *A61P 11/00* (2018.01); *A61P 11/06* (2018.01)

(58) Field of Classification Search
CPC .............................. A61K 31/425; A61P 11/00
USPC .................................................. 514/336, 364
See application file for complete search history.

(56) References Cited

U.S. PATENT DOCUMENTS

| | | |
|---|---|---|
| 7,414,037 B2 | 8/2008 | Verkman |
| 7,495,103 B2 | 2/2009 | Hadida |
| 8,124,781 B2 | 2/2012 | Siesel |
| 8,207,205 B2 | 6/2012 | Jones |
| 8,796,321 B2 | 8/2014 | Jones |
| 10,512,636 B2 | 12/2019 | McCarty |
| 10,555,918 B2 | 2/2020 | McCarty |
| 2007/0078130 A1 | 4/2007 | Ansorge |
| 2007/0264196 A1 | 11/2007 | Ruah |
| 2009/0264441 A1 | 10/2009 | Jones |
| 2010/0144733 A1 | 6/2010 | Doyle |
| 2011/0105565 A1 | 5/2011 | Verkman |
| 2011/0119775 A1 | 5/2011 | Verkman |
| 2012/0101143 A1 | 4/2012 | Verkman |
| 2014/0100155 A1 | 4/2014 | Madden |
| 2015/0011420 A1 | 1/2015 | Beekman |
| 2015/0139915 A1 | 5/2015 | Worgall |
| 2018/0147190 A1 | 5/2018 | McCarty |
| 2020/0085796 A1 | 3/2020 | McCarty |
| 2020/0138752 A1 | 5/2020 | McCarty et al. |

FOREIGN PATENT DOCUMENTS

| | | |
|---|---|---|
| WO | 2007112015 | 10/2007 |
| WO | 2008121877 | 10/2008 |
| WO | 2011133951 | 10/2011 |
| WO | 2013019169 | 2/2013 |
| WO | 2013173595 | 11/2013 |
| WO | 2014047212 | 3/2014 |
| WO | 2015011086 | 1/2015 |
| WO | 2015138909 | 9/2015 |

OTHER PUBLICATIONS

Barry et al. Cystic Fibrosis Transmembrane Conductance Regulator Modulators: The End of the Beginning, Semin Respir Crit Care Med 2015, 36:287-298.
Brown et al. Loss of cystic fibrosis transmembrane conductance regulator impairs lung endothelial cell barrier function and increases susceptibility to microvascular damage from cigarette smoke, Pulm Circ 2014, 4(2):260-268.
Caldwell et al. Increased folding and channel activity of a rare cystic fibrosis mutant with CFTR modulators, Am J Physiol Lung Cell Mol Physiol. 2011, 301(3): L346-L352.
Clunes et al. Cigarette smoke exposure induces CFTR internalization and insolubility, leading to airway surface liquid dehydration, FASEB J. 2012, 26(2):533-45.
Cui et al. Murine and human CFTR exhibit different sensitivities to CFTR potentiators, Am J Physiol Lung Cell Mol Physiol. 2015, 309(7): L687-L699.
Cui et al. Potentiators exert distinct effects on human, murine, and Xenopus CFTR, Am J Physiol Lung Cell Mol Physiol. 2016, 311(2): L192-L207.
Dransfield et al. Acquired Cystic Fibrosis Transmembrane Conductance Regulator Dysfunction in the Lower Airways in COPD, CHEST, 144(2):498-506.
Raju et al. Acquired CFTR Dysfunction in Chronic Bronchitis and Other Diseases of Mucus Clearance, Clin Chest Med. 2016, 37(1): 147-158.

(Continued)

*Primary Examiner* — Kevin E Weddington
(74) *Attorney, Agent, or Firm* — Emory Patent Group

(57) ABSTRACT

This disclosure relates to methods of treating or preventing cystic fibrosis transmembrane conductance regulator (CFTR) mediated diseases such as cystic fibrosis, chronic obstructive pulmonary disease, chronic pancreatitis, chronic bronchitis, asthma, mucus formation, comprising administering an effective amount of a 3-(phenyl)-N-(4-phenoxybenzyl)-1,2,4-oxadiazole-5-carboxamide compound, salt, or derivative thereof to a subject in need thereof. In certain embodiments, the 2-amino-N'-benzylidene-acetohydrazide compound is 3-(3,5-dibromo-4-hydroxyphenyl)-N-(4-phenoxybenzyl)-1,2,4-oxadiazole-5-carboxamide.

20 Claims, 4 Drawing Sheets

Specification includes a Sequence Listing.

(56) References Cited

OTHER PUBLICATIONS

Raju et al.The Cystic Fibrosis Transmembrane Conductance Regulator Potentiator Ivacaftor Augments Mucociliary clearance Abrogating Cystic Fibrosis Transmembrane Conductance Regulator Inhibition by Cigarette Smoke, Am J Respir Cell Mol Biol vol. 56, Iss 1, pp. 99-108, 2017.
Schwertschlag et al. Pharmacokinetics and Tolerability of iOWH032, an Inhibitor of the Cystic Fibrosis Transmembrane Conductance Regulator (CFTR) Chloride Channel, in Normal Volunteers and Cholera Patients, Mo1675, Gastroenterology 146(5):S-633.
Solomon et al. The therapeutic potential of CFTR modulators for COPD and other airway diseases, Curr Opin Pharmacol. 2017, 34: 132-139.
Stauffer et al. Bacterial Sphingomyelinase is a State-Dependent Inhibitor of the Cystic Fibrosis Transmembrane conductance Regulator (CFTR), Scientific Reports, 2017, 7:2931.
Thiagarajah et al. CFTR Inhibitors for Treating Diarrheal Disease, Clin Pharmacol Ther. 2012, 92(3): 287-290.
Yang et al. Small-Molecule CFTR Inhibitors Slow Cyst Growth in Polycystic Kidney Disease, J Am Soc Nephrol. 2008, 19(7): 1300-1310.
Extended European Search Report for EP Application No. 16804126.7 dated Nov. 22, 2018.
Extended European Search Report, 16804124.2—1109 / 3302455 PCT/US2016034662, dated Dec. 20, 2018.
Muanprasat et al. Discovery of Glycine Hydrazide Pore-occluding CFTR Inhibitors: Mechanism, Structure—Activity Analysis, and in Vivo Efficacy, J Gen Physiol, 2004,124(2)125-37.

SEQUENCE LISTING

```
<160> NUMBER OF SEQ ID NOS: 1

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30
```

-continued

Glu Leu Ser Asp Ile Tyr Gln Ile Pro Ser Val Asp Ser Ala Asp Asn
                35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
                115                 120                 125

Leu Leu Phe Ile Val Arg Thr Leu Leu Leu His Pro Ala Ile Phe Gly
                130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
                195                 200                 205

Ala Leu Leu Met Gly Leu Ile Trp Glu Leu Leu Gln Ala Ser Ala Phe
                210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
                275                 280                 285

Arg Gln Thr Glu Leu Lys Leu Thr Arg Lys Ala Ala Tyr Val Arg Tyr
                290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
                355                 360                 365

Asn Lys Ile Gln Asp Phe Leu Gln Lys Gln Glu Tyr Lys Thr Leu Glu
                370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
                435                 440                 445

Glu Arg Gly Gln Leu Leu Ala Val Ala Gly Ser Thr Gly Ala Gly Lys

```
                    450                 455                 460
Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                    485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
                530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
                595                 600                 605

His Leu Lys Lys Ala Asp Lys Ile Leu Ile Leu His Glu Gly Ser Ser
                610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
                690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
                755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Phe Phe Asp Asp Met Glu Ser Ile Pro Ala Val Thr Thr Trp Asn Thr
                835                 840                 845

Tyr Leu Arg Tyr Ile Thr Val His Lys Ser Leu Ile Phe Val Leu Ile
                850                 855                 860

Trp Cys Leu Val Ile Phe Leu Ala Glu Val Ala Ala Ser Leu Val Val
865                 870                 875                 880
```

```
Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275
```

```
Leu Gln Gln Trp Arg Lys Ala Phe Gly Val Ile Pro Gln Lys Val
    1280            1285                1290

Phe Ile Phe Ser Gly Thr Phe Arg Lys Asn Leu Asp Pro Tyr Glu
    1295            1300                1305

Gln Trp Ser Asp Gln Glu Ile Trp Lys Val Ala Asp Glu Val Gly
    1310            1315                1320

Leu Arg Ser Val Ile Glu Gln Phe Pro Gly Lys Leu Asp Phe Val
    1325            1330                1335

Leu Val Asp Gly Gly Cys Val Leu Ser His Gly His Lys Gln Leu
    1340            1345                1350

Met Cys Leu Ala Arg Ser Val Leu Ser Lys Ala Lys Ile Leu Leu
    1355            1360                1365

Leu Asp Glu Pro Ser Ala His Leu Asp Pro Val Thr Tyr Gln Ile
    1370            1375                1380

Ile Arg Arg Thr Leu Lys Gln Ala Phe Ala Asp Cys Thr Val Ile
    1385            1390                1395

Leu Cys Glu His Arg Ile Glu Ala Met Leu Glu Cys Gln Gln Phe
    1400            1405                1410

Leu Val Ile Glu Glu Asn Lys Val Arg Gln Tyr Asp Ser Ile Gln
    1415            1420                1425

Lys Leu Leu Asn Glu Arg Ser Leu Phe Arg Gln Ala Ile Ser Pro
    1430            1435                1440

Ser Asp Arg Val Lys Leu Phe Pro His Arg Asn Ser Ser Lys Cys
    1445            1450                1455

Lys Ser Lys Pro Gln Ile Ala Ala Leu Lys Glu Glu Thr Glu Glu
    1460            1465                1470

Glu Val Gln Asp Thr Arg Leu
    1475            1480
```

3-(PHENYL)-N-(4-PHENOXYBENZYL)-1,2,4-OXADIAZOLE-5-CARBOXAMIDE COMPOUNDS FOR THE MANAGEMENT OF CFTR PROTEIN MEDIATED DISEASES

CROSS-REFERENCE TO RELATED APPLICATIONS

This application is a division of U.S. patent application Ser. No. 15/578,159 filed Nov. 29, 2017, which is the National Stage of International Application No. PCT/US2016/034682 filed May 27, 2016, which claims the benefit of U.S. Provisional Application No. 62/167,999 filed May 29, 2015. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15087USDIV_ST25.txt. The text file is 13 KB, was created on Nov. 22, 2019, and is being submitted electronically via EFS-Web.

BACKGROUND

Cystic fibrosis (CF) is a lethal, recessive, genetic disease caused by mutations in the cystic fibrosis transmembrane conductance regulator (CFTR) protein. The cystic fibrosis CFTR protein functions as a cell surface ion channel. Mutations of CFTR are thought to reduce cell surface expression and/or the ion transport function. This causes decreased water secretion by cells and ultimately thicker mucus layers lining the membranes in the lungs and other parts of the body. In addition to cystic fibrosis, certain CFTR mutations cause recurrent acute and chronic pancreatitis. As an inherited disease, there is no cure for cystic fibrosis; thus, there is a need to identify improved therapies.

Ivacaftor is indicated for the treatment of cystic fibrosis and acts as a potentiator of CFTR by enhancing ion channel transport. Ivacaftor is also approved for treatment in combination with lumacaftor for patients who have a deletion of the codon for phenylalanine (F) at position 508, referred to as the F508-del mutation. Having the F508-del mutation reduces escape of CFTR from the endoplasmic reticulum. Lumacaftor is reported to increase the trafficking of CFTR to the cell surface. The combination of Ivacaftor and lumacaftor is also approved for patients with other CFTR mutations.

Hostos et al. report the compound iOWHO32 is a synthetic CFTR inhibitor for use to treat infectious diarrhea. Future Med. Chem. 2011, 3(10): 1317-1325. See also U.S. Patent Application Publications 2015/139915, 2011/288093, 2011/288103, and 2009/318429.

The activities of CFTR channels were also identified to be modulated by several other compounds. Potentiators include P1 (VRT-532), P2 (PG-01), and P3 (SF-03). See Caldwell et al., Increased folding and channel activity of a rare cystic fibrosis mutant with CFTR modulators, Am J Physiol Lung Cell Mol Physiol, 2011, 301(3):L346-52. Other CFTR altering compounds include GlyH-101, NPPB, and glibenclamide. See Cui et al., Murine and human CFTR exhibit different sensitivities to CFTR potentiators, Am J Physiol Lung Cell Mol Physiol, 2015, 309(7):L687-99.

Dransfield et al. report acquired CFTR dysfunction in the lower airways in chronic obstructive pulmonary disease (COPD). Chest. 2013, 144(2):498-506. Raju et al. report acquired CFTR dysfunction in chronic bronchitis and other conditions of mucus clearance. Clin Chest Med, 2016, 37 147-158.

Yang et al. report that molecules that inhibit CFTR slow cyst growth in polycystic kidney disease. J Am Soc Nephrol, 2008, 19(7): 1300-1310.

Thiagarajah & Verkman report CFTR inhibitors for treating diarrheal disease. Clin Pharmacol Ther, 2012, 92(3):287-90.

References cited herein are not an admission of prior art.

SUMMARY

Figure 1:
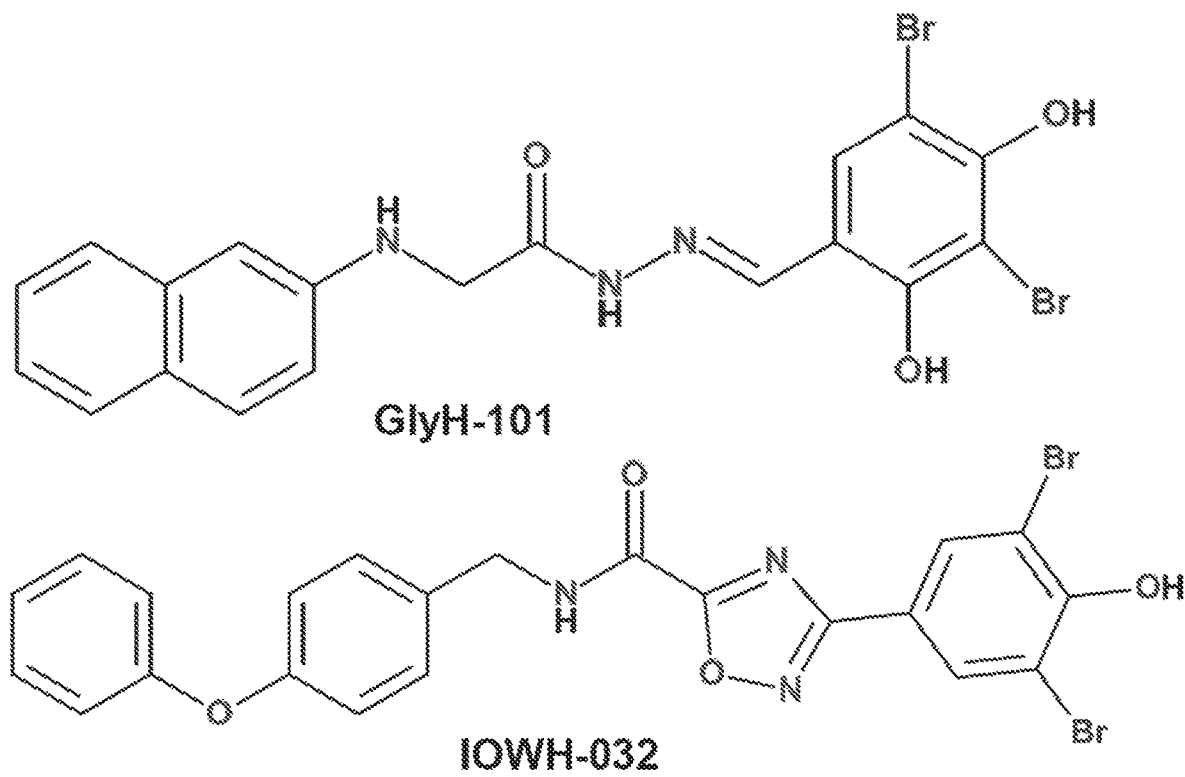
FIG. 1 illustrates the chemical structures of iOWH-032 and GlyH-101.

This disclosure relates to methods of treating or preventing cystic fibrosis transmembrane conductance regulator (CFTR) mediated diseases such as cystic fibrosis, chronic obstructive pulmonary disease, chronic pancreatitis, chronic bronchitis, asthma, the formation of mucus, or conditions associated therewith comprising administering an effective amount of a 3-(phenyl)-N-(4-phenoxybenzyl)-1,2,4-oxadiazole-5-carboxamide compound, salt, or derivative thereof to a subject in need thereof.

In certain embodiments, the 3-(phenyl)-N-(4-phenoxybenzyl)-1,2,4-oxadiazole-5-carboxamide compound, salt, or derivative is 3-(3,5-dibromo-4-hydroxyphenyl)-N-(4-phenoxybenzyl)-1,2,4-oxadiazole-5-carboxamide.

In certain embodiments, the disclosure relates to methods of treating or preventing pancreatic dysfunction, such as recurrent, acute, or chronic pancreatitis, comprising administering an effective amount of a 3-(phenyl)-N-(4-phenoxybenzyl)-1,2,4-oxadiazole-5-carboxamide compound, salt, or derivative thereof to a subject in need thereof.

In certain embodiments, the subject is exhibiting symptoms or, at risk of, or diagnosed with cystic fibrosis, chronic obstructive pulmonary disease, chronic bronchitis, asthma, recurrent, acute, or chronic pancreatitis.

In certain embodiments, the 3-(phenyl)-N-(4-phenoxybenzyl)-1,2,4-oxadiazole-5-carboxamide compound, salt, or derivative is administered in combination with another therapeutic agent, such as lumacaftor or other compound that potentiates CFTR and/or increases cell surface expression. In certain embodiments, the 3-(phenyl)-N-(4-phenoxybenzyl)-1,2,4-oxadiazole-5-carboxamide compound, salt, or derivative is administered in combination with pancreatic enzyme supplements, anti-bacterial agents, anti-viral agents, anti-inflammatory agents, and/or mucus reducing agents.

In certain embodiments, the disclosure relates to pharmaceutical composition comprising a compound disclosed herein and a pharmaceutically acceptable excipient. In certain embodiments, the pharmaceutical composition is in the form of a pill, tablet, aerosol, or capsule or an aqueous buffer solution, typically a saline phosphate buffer between a pH of 6 to 8, optionally comprising a saccharide or polysaccharide.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Certain of the compounds described herein may contain one or more asymmetric centers and may give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, tautomer forms, hydrated forms, optically substantially pure forms and intermediate mixtures.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers to an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C═O)alkyl).

"Alkylsulfonyl" refers to an alkyl as defined above attached through a sulfonyl bridge (i.e., —S(═O)$_2$alkyl) such as mesyl and the like, and "Arylsulfonyl" refers to an aryl attached through a sulfonyl bridge (i.e., —S(═O)$_2$aryl).

"Alkylsulfinyl" refers to an alkyl as defined above attached through a sulfinyl bridge (i.e. —S(═O)alkyl).

"Aminoalkyl" refers to an amino group attached through an alkyl bridge. An example of an aminoalkyl is aminomethyl, (i.e., NH$_2$—CH$_2$—).

"Hydroxyalkyl" refers to a hydroxy group attached through an alkyl bridge. An example of a hydroxyalkyl is hydroxyethyl, (i.e., HO—CH$_2$CH$_2$—).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Typical prodrugs are pharmaceutically acceptable esters. Prodrugs include compounds wherein a hydroxyl, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxyl group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments of the present disclosure also contemplate treatment that merely reduces symptoms, and/or delays disease progression.

As used herein, the term "effective amount" of a compound, with respect to the administration for treatment or preventative methods, refers to an amount of the compound which, when delivered as part of desired dose regimen, brings about management of the disease or disorder to clinically acceptable standards considering a subject physical attributes such as weight, age, etc.

As used herein, the term "combination with" when used to describe administration with an additional treatment means that the agent may be administered prior to, together with, or after the additional treatment, or a combination thereof.

The term "CFTR" refers to refers to the naturally occurring molecule in humans identified as having (SEQ ID NO: 1) or variants thereof.

```
MQRSPLEKASVVSKLFFSWTRPILRKGYRQRLELSDIYQIPSVDSADN
LSEKLEREWDRELASKKNPKLINALRRCFFWRFMFYGIFLYLGEVTKA
VQPLLLGRIIASYDPDNKEERSIAIYLGIGLCLLFIVRTLLLHPAIFG
LHHIGMQMRIAMFSLIYKKTLKLSSRVLDKISIGQLVSLLSNNLNKFD
EGLALAHFVWIAPLQVALLMGLIWELLQASAFCGLGFLIVLALFQAGL
GRMMMKYRDQRAGKISERLVITSEMIENIQSVKAYCWEEAMEKMIENL
RQTELKLTRKAAYVRYFNSSAFFFSGFFVVFLSVLPYALIKGIILRKI
FTTISFCIVLRMAVTRQFPWAVQTWYDSLGAINKIQDFLQKQEYKTLE
YNLTTTEVVMENVTAFWEEGFGELFEKAKQNNNNRKTSNGDDSLFFSN
FSLLGTPVLKDINFKIERGQLLAVAGSTGAGKTSLLMVIMGELEPSEG
KIKHSGRISFCSQFSWIMPGTIKENIIFGVSYDEYRYRSVIKACQLEE
DISKFAEKDNIVLGEGGITLSGGQRARISLARAVYKDADLYLLDSPFG
YLDVLTEKEIFESCVCKLMANKTRILVTSKMEHLKKADKILILHEGSS
YFYGTFSELQNLQPDFSSKLMGCDSFDQFSAERRNSILTETLHRFSLE
GDAPVSWTETKKQSFKQTGEFGEKRKNSILNPINSIRKFSIVQKTPLQ
MNGIEEDSDEPLERRLSLVPDSEQGEAILPRISVISTGPTLQARRRQS
VLNLMTHSVNQGQNIHRKTTASTRKVSLAPQANLTELDIYSRRLSQET
GLEISEEINEEDLKECFFDDMESIPAVTTWNTYLRYITVHKSLIFVLI
WCLVIFLAEVAASLVVLWLLGNTPLQDKGNSTHSRNNSYAVIITSTSS
YYVFYIYVGVADTLLAMGFFRGLPLVHTLITVSKILHHKMLHSVLQAP
MSTLNTLKAGGILNRFSKDIAILDDLLPLTIFDFIQLLLIVIGAIAVV
AVLQPYIFVATVPVIVAFIMLRAYFLQTSQQLKQLESEGRSPIFTHLV
TSLKGLWTLRAFGRQPYFETLFHKALNLHTANWFLYLSTLRWFQMRIE
MIFVIFFIAVTFISILTTGEGEGRVGIILTLAMNIMSTLQWAVNSSID
```
-continued
```
VDSLMRSVSRVFKFIDMPTEGKPTKSTKPYKNGQLSKVMIIENSHVKK
DDIWPSGGQMTVKDLTAKYTEGGNAILENISFSISPGQRVGLLGRTGS
GKSTLLSAFLRLLNTEGEIQIDGVSWDSITLQQWRKAFGVIPQKVFIF
SGTFRKNLDPYEQWSDQEIWKVADEVGLRSVIEQFPGKLDFVLVDGGC
VLSHGHKQLMCLARSVLSKAKILLLDEPSAHLDPVTYQIIRRTLKQAF
ADCTVILCEHRIEAMLECQQFLVIEENKVRQYDSIQKLLNERSLFRQA
ISPSDRVKLFPHRNSSKCKSKPQIAALKEETEEEVQDTRL.
```

Managing Cystic Fibrosis Transmembrane Conductance Regulator (CFTR) Protein Mediated Diseases or Conditions Cystic fibrosis (CF) is caused by mutations in the cystic fibrosis transmembrane conductance regulator (CFTR). CFTR is a member of the ABC Transporter Superfamily, and functions as a chloride ion channel. Experimental data and available homology models suggest that CFTR contains five functional domains: two membrane-spanning domains (MSDs) with six transmembrane helices (TM) in each MSD, two nucleotide-binding domains (NBD1, NBD2), and a unique regulatory (R) domain containing multiple protein kinase A (PKA) and C (PKC) consensus sites. In addition to the human gene, CFTR clones have been produced from other species, including *Xenopus laevis* (frog), pig, mouse, and sheep.

CFTR is regulated by ATP and PKA. The activities of CFTR channels can be modulated by certain compounds. These could be broadly divided into CFTR potentiators, CFTR correctors, and CFTR blockers. Some CFTR blockers have also been found to bear potentiator function. These include GlyH-101, NPPB, and glibenclamide. NPPB, an hCFTR blocker, was discovered to potentiate hCFTR when the channel is incompletely phosphorylated, i.e., when activated by a low concentration of PKA. Extremely high concentrations of NPPB were also reported to potentiate hCFTR. The hCFTR blockers GlyH-101 and glibenclamide also potentiate mCFTR.

Efforts towards the development of CFTR potentiators have led to the identification of the drug with the generic name ivacaftor (also called VX-770 with the trade name Kalydeco™). Ivacaftor is also approved in combination with lumacaftor for patients who have deletion of the codon for phenylalanine (F) at position 508, referred to as the F508 del mutation, which is the most common CFTR mutation found in patients. Having the F508 del mutation reduces escape of CFTR from the endoplasmic reticulum. Lumacaftor is reported to increase the trafficking of CFTR to the cell surface.

Mutations in the CFTR gene result in absence or dysfunction of the protein that regulates ion transport across the apical membrane at the surface of certain epithelia. Although CFTR functions mainly as a chloride channel, it has other roles, including inhibition of sodium transport through the epithelial sodium channel, regulation of the outwardly rectifying chloride channel, intracellular vesicle transport, and inhibition of endogenous calcium-activated chloride channels. CFTR is also involved in bicarbonate transport. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths.

Although it is not intended that embodiments of this disclosure be limited by any particular mechanism, a compound disclosed herein may increase chloride transport of a CFTR protein in a cell by increasing the CFTR protein channel gating, by increasing the amount of CFTR protein that is trafficked to the cell surface, or a combination thereof. In some embodiments, the compound increases chloride transport by increasing the amount of CFTR protein that is trafficked to the cell surface. In some embodiments, the compound increases chloride transport by both increasing the CFTR protein channel gating and by increasing the amount of CFTR protein that is trafficked to the cell surface.

Compounds of this disclosure are useful as modulators of CFTR and treating diseases or disorders mediated by CFTR such as for the treatment of disease, disorders or conditions such as cystic fibrosis, asthma, constipation, pancreatitis, gastrointestinal diseases or disorders, infertility, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/Pseudo-Hurler, mucopolysaccharidoses, Sandhof/Tay-Sachs, Crigler-Najjar type II, polyendocrinopathy, hyperinsulemia, diabetes mellitus, laron dwarfism, myeloperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentororubal pallidoluysian, and myotic dystrophy, as well as spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome, spongiform encephalopathies, such as Hereditary Creutzfeldt-Jakob disease (due to Prion protein processing defect), Fabry disease and Straussler-Scheinker syndrome.

With respect to a compound or combinations of compounds ability to potentiate or increase chloride transport of a CFTR protein, this may be determined by utilizing standard assays known in the art, including, but not limited to, the utilization of Using chamber recordings or animal models. Using chamber assays use electrodes to measure ion flow across the membranes of cells grown into a monolayer with tight junctions. One obtains and grows primary CF airway epithelial cells. Two days before an Using assay, one aspirates the mucus on the apical surface of the cells. One day before the Using assay test, one adds compounds to the basolateral surface of the cells at various test concentrations dissolved in solution. For the Using experiment, one pre-equilibrates a cell containing chamber buffer solution on both apical and basolateral sides by bubbling with room air to facilitate mixing upon addition of compounds. One records a resting current to ensure a stable baseline. One blocks the resting current by the apical addition of benzamil, an ENaC inhibitor. After several minutes, one adds forskolin to both the apical and basolateral side to stimulate CFTR. One detects an increase in chloride current as an upward deflection of the trace. After an additional about of time, one adds a test compound wherein a potentiator further increasing the chloride current.

The methods and compounds described herein may be tested in any one of several animal models in order to further characterize the compound, or in order to optimize dosing or for the generation of formulations.

Mouse models having null or mutant forms of CFTR exist. See, e.g., Fisher et al., 2011, Methods Mol Biol, 742:311-34. These mouse models recapitulate various CF-related organ pathologies to varying degrees, and the severity of the phenotypes of these mice are generally based on the amounts of CFTR mRNA present. Most of the mouse models display phenotypes such as severe abnormalities of the gastrointestinal tract, failure to thrive, decreased survival and hyperinflammatory responses in the airway. These mice also may display defects in cAMP-inducible chloride permeability in the nasal epithelium, decreased mucociliary clearance, reduced fertility, mild pancreatic dysfunction and liver abnormalities. Typically, these mouse models do not display the significant spontaneous lung disease as observed in CF human subjects.

A pig and ferret model of CF have been developed. See, e.g., Keiser, et al., 2011, Curr Opin Pulm Medic, 17: 478-483. These models recapitulate the CF symptoms observed in human subjects. In particular, a pig having a CFTR F508del/F508del mutation develops lung disease and severe gallbladder disease and displays exocrine pancreatic defects and hepatic lesions. In some embodiments, a compound disclosed herein is administered to the CFTR F508del/F508del pig, and effects of the compound on CF-like symptoms are assessed.

Personalized Medicine

In some embodiments, the methods of the disclosure comprises treating a subject having mutation in CFTR of SEQ ID NO: 1. In some embodiments, the subject to be treated with a compound disclosed herein is diagnosed or identified through testing, determining or measuring a nucleic acid or associated protein as having one or more CFTR mutations. In some embodiments the mutations are R352A, E56K, P67L, E92K, R117H, L206W and/or DELTA F508.

In some embodiments, the methods of the disclosure comprises treating a subject having one or more mutations is at an amino acid position corresponding to any one of, or combination of, amino acid residues 92, 126, 130, 132, 137, 138, 139, 140, 141, 145, 146, 165, 166, 170, 175, 177, 178, 179, 206, 241, 243, 244, 248, 258, 277, 279, 281, 285, 287, 353, 355, 356, 357, 360, 361, 364, 365, 360, 373, 375, 378, 379, 383, 388, 392, or 394 of SEQ ID NO: 1. In some embodiments, in addition to the mutations listed, the mutant CFTR protein further comprises a mutation at a position corresponding to 508 of SEQ ID NO: 1. In some embodiments the mutation at a position corresponding to 508 of SEQ ID NO: 1 is DELTA F508. In some embodiments, the mutation is selected from the group consisting of a substitution of lysine or leucine for glutamic acid at amino acid residue 56 of SEQ ID NO: 1. In some embodiments, the mutation is the substitution of leucine for proline at amino acid residue 67 of SEQ ID NO: 1. In some embodiments, the mutation is selected from the group consisting of a substitution of lysine, glutamine, arginine, valine or aspartic acid for glutamic acid at amino acid residue 92 of SEQ ID NO: 1. In some embodiments, the mutation is the substitution of an aspartic acid for glycine at amino acid residue 126 of SEQ ID NO: 1. In some embodiments, the mutation is a substitution of valine for leucine at amino acid residue 130 of SEQ ID NO: 1. In some embodiments, the mutation is a substitution of methionine for isoleucine at amino acid 132 of SEQ ID NO: 1. In some embodiments, the mutation is a substitution of histidine, proline or arginine for leucine at amino acid 137 residue of SEQ ID NO: 1. In some embodiments, the mutation is an insertion of leucine at amino acid residue 138 of SEQ ID NO: 1. In some embodiments, the mutation is a substitution of leucine or arginine for histidine at amino acid residue 139 of SEQ ID NO: 1. In some embodiments, the mutation is a substitution of serine or leucine for proline at amino acid residue 140 of SEQ ID NO: 1. In some embodiments, the mutation is a substitution of aspartic acid for alanine at amino acid residue 141 of SEQ ID NO: 1. In some embodiments, the mutation is a substitution of histidine for leucine at amino acid residue 145 of SEQ ID NO: 1. In some embodiments, the mutation is a substitution of arginine for histidine at amino acid residue 146 of SEQ ID NO: 1. In some embodiments, the mutation is a substitution of serine for leucine at amino acid residue 165 of SEQ ID NO: 1. In some embodiments, the mutation is a substitution of glutamine for lysine at amino acid residue 166 of SEQ ID NO: 1. In some embodiments, the mutation is a substitution of cysteine, glycine, or histidine for arginine at amino acid residue 170 of SEQ ID NO: 1. In some embodiments, the mutation is a substitution of valine for isoleucine at amino acid residue 175 of SEQ ID NO: 1. In some embodiments, the mutation is a substitution of threonine for isoleucine at amino acid residue 177 of SEQ ID NO: 1. In some embodiments, the mutation is a substitution of glutamic acid or arginine for glycine at amino acid residue 178 of SEQ ID NO: 1. In some embodiments, the mutation is a substitution of lysine for glutamine at amino acid residue 179 of SEQ ID NO: 1. In some embodiments, the mutation is a substitution of tryptophan for leucine at amino acid residue 206 of SEQ ID NO:1. IN some embodiments, the mutation is a substitution of aspartic acid for valine at amino acid residue 232 of SEQ ID NO: 1. In some embodiments, the mutation is a substitution of arginine for glycine at amino acid residue 241 of SEQ ID NO: 1. In some embodiments, the mutation is a substitution of leucine for methionine at amino acid residue 243 of SEQ ID NO: 1. In some embodiments, the mutation is a substitution of lysine for methionine at amino acid residue 244 of SEQ ID NO: 1. In some embodiments, the mutation is a substitution of threonine for arginine at amino acid residue 248 of SEQ ID NO: 1. In some embodiments, the mutation is a substitution of glycine for arginine at amino acid residue 258 of SEQ ID NO: 1. In some embodiments, the mutation is a substitution of arginine for tryptophan at amino acid residue 277 of SEQ ID NO: 1. In some embodiments, the mutation is a substitution of aspartic acid for glutamic acid at amino acid residue 279 of SEQ ID NO: 1. In some embodiments, the mutation is a substitution of threonine for methionine at amino acid residue 281 of SEQ ID NO: 1. In some embodiments, the mutation is a substitution of phenylalanine for isoleucine at amino acid residue 285 of SEQ ID NO: 1. In some embodiments, the mutation is a substitution of tyrosine for asparagine at amino acid residue 287 of SEQ ID NO: 1. In some embodiments, the mutation is a substitution of lysine for isoleucine at amino acid residue 336 of SEQ ID NO: 1. In some embodiments, the mutation is a substitution of histidine for glutamine at amino acid residue 353 of SEQ ID NO: 1. In some embodiments, the mutation is a substitution of serine for proline at amino acid residue 355 of SEQ ID NO: 1. In some embodiments, the mutation is a substitution of serine for tryptophan at amino acid residue 356 of SEQ ID NO: 1. In some embodiments, the mutation is a substitution of lysine or arginine for glutamine at amino acid residue 359 of SEQ ID NO: 1. In some embodiments, the mutation is a substitution of lysine or arginine for threonine at amino acid residue 360 of SEQ ID NO: 1. In some embodiments, the mutation is a substitution of arginine for tryptophan at amino acid residue 361 of SEQ ID NO: 1. In some embodiments, the mutation is a substitution of serine for proline at amino acid residue 364 of SEQ ID NO: 1. In some embodiments, the mutation is a substitution of leucine for proline at amino acid residue 365 of SEQ ID NO: 1. In some embodiments, the mutation is the insertion of aspartic acid and lysine after amino acid residue 370 of SEQ ID NO: 1. In some embodiments, the mutation is a substitution of glutamic acid for aspartic acid at amino acid residue 373 of SEQ ID NO: 1. In some embodiments, the mutation is a substitution of phenylalanine for leucine at amino acid residue 375 of SEQ ID NO: 1. In some embodiments, the mutation is a substitution of arginine for glutamine at amino acid residue 378 of SEQ ID NO: 1. In some embodiments, the mutation is a substitution of lysine for glutamic acid at amino acid residue 379 of SEQ ID NO: 1. In some embodiments, the mutation is a substitution of serine for leucine at amino acid residue 383 of SEQ ID NO: 1. In some embodiments, the mutation is a substitution of methionine for threonine at amino acid residue 388 of SEQ ID NO: 1. In some embodiments, the mutation is a substitution of alanine or glycine for valine at amino acid residue 392 of SEQ ID NO: 1. In some embodiments, the mutation is a substitution of arginine for methionine at amino acid residue 394 of SEQ ID NO: 1. In some embodiments, the mutation is the substation of glutamic acid for alanine at amino acid residue 455 of SEQ ID NO: 1. In some embodiments, the mutation is the substitution of aspartic acid for histidine at amino acid residue 1054 of SEQ ID NO: 1. In some embodiments, the mutation is the substitution of arginine for glycine at amino acid residue 1061 of SEQ ID NO: 1. In some embodiments, the mutation is the substitution of histidine for arginine at amino acid residue 1066 of SEQ ID NO: 1. In some embodiments, the mutation is the substitution of leucine for phenylalanine at amino acid residue 1074 of SEQ ID NO: 1. In some embodiments, the mutation is the substitution of arginine for histidine at amino acid residue 1085 of SEQ ID NO: 1.

In some embodiments, the methods of the disclosure comprises treating a subject having one or more CFTR mutations selected from G551D, G1244E, G1349D, G178R, G551S, S1251N, S1255P, S549N, or S549R of SEQ ID NO: 1.

Combination Therapies

The compounds of this disclosure may be administered in combination with other pharmaceutical agents such as antibiotics, anti-viral agents, anti-inflammatory agents, bronchodilators, or mucus-thinning medicines. In particular antibiotics for the treatment of bacteria mucoid *Pseudomonas* may be used in combination with compounds disclosed herein.

Inhaled antibiotics such as tobramycin, colistin, and aztreonam can be used in combination with treatment with compounds disclosed herein. Anti-inflammatory medicines may also be used in combination with compounds disclosed herein to treat CFTR related diseases. Bronchodilators can be used in combination with compounds disclosed herein to treat CFTR related diseases.

In one embodiment, the disclosure relates to combination therapy comprising compounds disclosed herein and other pharmaceutical agents useful for the treatment of CF. In a preferred embodiment, the aminoglycoside gentamicin can be used. In a preferred embodiment, ataluren, ivacaftor or lumacaftor may be used in combination with compounds disclosed herein.

In some embodiments, the method comprises administering to a subject a compound disclosed herein and at least one additional therapeutic agent. In some embodiments, the additional therapeutic agent is a bronchodilator, an antibiotic, a mucolytic agent, a nutritional agent or an agent that blocks ubiquitin-mediated proteolysis.

In certain embodiments, a bronchodilator for use as an additional therapeutic agent may be a short-acting beta2 agonist, a long-acting beta2 agonist or an anticholinergic. In some embodiments, the bronchodilator is any one of, or combination of, salbutamol/albuterol, levosalbutamol/levalbuterol, pirbuterol, epinephrine, ephedrine, terbutaline, salmeterol, clenbuterol, formoterol, bambuterol, indacaterol, theophylline, tiotropium or ipratropium bromide.

In certain embodiments, an antibiotic for use as an additional therapeutic agent may be any antibiotic chosen by a physician for reducing lung infections in a CF subject. In some embodiments, the antibiotic is any one of, or combination of, xicillin, clavulanate potassium, aztreonam, ceftazidime, ciprofloxacin, gentamicin or tobramycin.

In certain embodiments, a mucolytic agent for use as an additional therapeutic agent may be any agent used for breaking down the gel structure of mucus and therefore decreasing its elasticity and viscosity. In some embodiments, the mucolytic agent is N-acetylcysteine, dornase alpha, hypertonic solution, mannitol, gelsolin or thymosin-beta4.

A nutritional agent for use as an additional therapeutic agent may be any agent that may be used to promote adequate growth and weight gain in a CF subject. In some embodiments, the nutritional agent is any one of, or combination of, vitamins A, D, E, or K, sodium chloride, calcium, or pancreatic enzymes. In some embodiments, the nutritional agent is a multivitamin. In some embodiments, the nutritional agent is a high calorie food or food supplement.

An agent that blocks ubiquitin-mediated proteolysis for use as an additional therapeutic agent is any agent that blocks proteasomal degradation of misfolded CFTR. In some embodiments, the agent that blocks ubiquitin-mediated proteolysis is a proteasome inhibitor. In some embodiments, the agent that blocks ubiquitin-mediated proteolysis is selected from the group consisting of bortezomib, carfilzomib, and marizomib.

3-(Phenyl)-N-(4-phenoxybenzyl)-1,2,4-oxadiazole-5-carboxamide Compounds and Derivatives A virtual screening of a database of commercially available compounds led to the identification of compounds with potentiator activity in vitro. In certain embodiments, this disclosure relates to 3-(phenyl)-N-(4-phenoxybenzyl)-1,2,4-oxadiazole-5-carboxamide compounds, salts, or derivatives thereof. In certain embodiments, the derivative is a compound of the following formula:

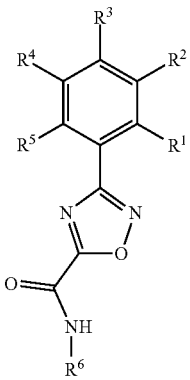

Formula I or salts, esters, prodrug, or derivatives thereof wherein, $R^1$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^1$ is optionally substituted with one or more, the same or different, $R^{10}$.

$R^2$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^2$ is optionally substituted with one or more, the same or different, $R^{10}$.

$R^3$ is hydrogen, alkyl, alkenyl, alkynyl, alkanoyl, alkoxyalkyl, halogen, bomo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^3$ is optionally substituted with one or more, the same or different, $R^{10}$.

$R^4$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^4$ is optionally substituted with one or more, the same or different, $R^{10}$.

$R^5$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^5$ is optionally substituted with one or more, the same or different, $R^{10}$.

$R^6$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^6$ is optionally substituted with one or more, the same or different, $R^{10}$; and $R^{10}$ is alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, benzyl, benzoyl, carbocyclyl, aryl, or heterocyclyl.

In certain embodiments, the $R^1$ is hydrogen.
In certain embodiments, the $R^5$ is hydroxyl.
In certain embodiments, the $R^4$ is halogen or bromo.
In certain embodiments, the $R^3$ is hydroxyl.
In certain embodiments, the $R^2$ is halogen or bromo.
In certain embodiments, the $R^6$ phenyl optionally ortho or para substituted.

In certain embodiments, this disclosure relates to 3-(phenyl)-N-(4-phenoxybenzyl)-1,2,4-oxadiazole-5-carboxamide compounds, salts, or derivatives thereof. In certain embodiments, the derivative is a compound of the following formula:

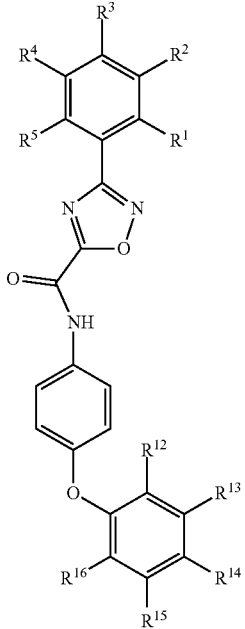

Formula IA or salts, esters, prodrug, or derivatives thereof wherein, $R^1$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^1$ is optionally substituted with one or more, the same or different, $R^{10}$;

$R^2$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^2$ is optionally substituted with one or more, the same or different, $R^{10}$;

$R^3$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^3$ is optionally substituted with one or more, the same or different, $R^{10}$;

$R^4$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^4$ is optionally substituted with one or more, the same or different, $R^{10}$;

$R^5$ is hydrogen, alkyl, alkenyl, alkynyl, alkanoyl, alkoxyalkyl, halogen, bromo, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^5$ is optionally substituted with one or more, the same or different, $R^{10}$;

$R^{10}$ is alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{10}$ is optionally substituted with one or more, the same or different, $R^{11}$;

$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, benzyl, benzoyl, carbocyclyl, aryl, or heterocyclyl;

$R^{12}$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{12}$ is optionally substituted with one or more, the same or different, $R^{20}$;

$R^{13}$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{13}$ is optionally substituted with one or more, the same or different, $R^{20}$;

$R^{14}$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{14}$ is optionally substituted with one or more, the same or different, $R^{20}$;

$R^{15}$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{15}$ is optionally substituted with one or more, the same or different, $R^{20}$;

$R^{16}$ is hydrogen, alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{16}$ is optionally substituted with one or more, the same or different, $R^{20}$;

$R^{20}$ is alkyl, alkenyl, alkynyl, alkanoyl, alkoxyalkyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, benzyl, benzoyl, carbocyclyl, aryl, or heterocyclyl.

In certain embodiments, the compound is 3-(3,5-dibromo-4-hydroxyphenyl)-N-(4-phenoxybenzyl)-1,2,4-oxadiazole-5-carboxamide or salt thereof.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

In certain embodiments, the pharmaceutical composition is in the form of a pill, tablet, capsule, gel, or particles. In certain embodiments, the pharmaceutical composition is in liquid form comprising oils, fatty acids, saturated or unsaturated hydrocarbons, or an aqueous buffer, e.g. phosphate buffer optionally comprising saline and/or a saccharide or polysaccharide.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

In certain embodiments, the pharmaceutical composition comprises a compound disclosed herein and a propellant. In certain embodiments, an aerosolizing propellant is compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising a compound herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxy groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

In certain embodiments, the disclosure relates to pharmaceutical composition comprising a compounds disclosed herein and a pharmaceutically acceptable excipient, such as a pharmaceutically acceptable excipient selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanuium dioxide, talc, corn starch, carnuba wax, stearic acid, sorbic acid, magnesium stearate, calcium stearate, castor oil, mineral oil, calcium phosphate, starch, carboxymethyl ether of starch, iron oxide, triacetin, acacia gum, esters or salts thereof.

Examples

Figure 2A:
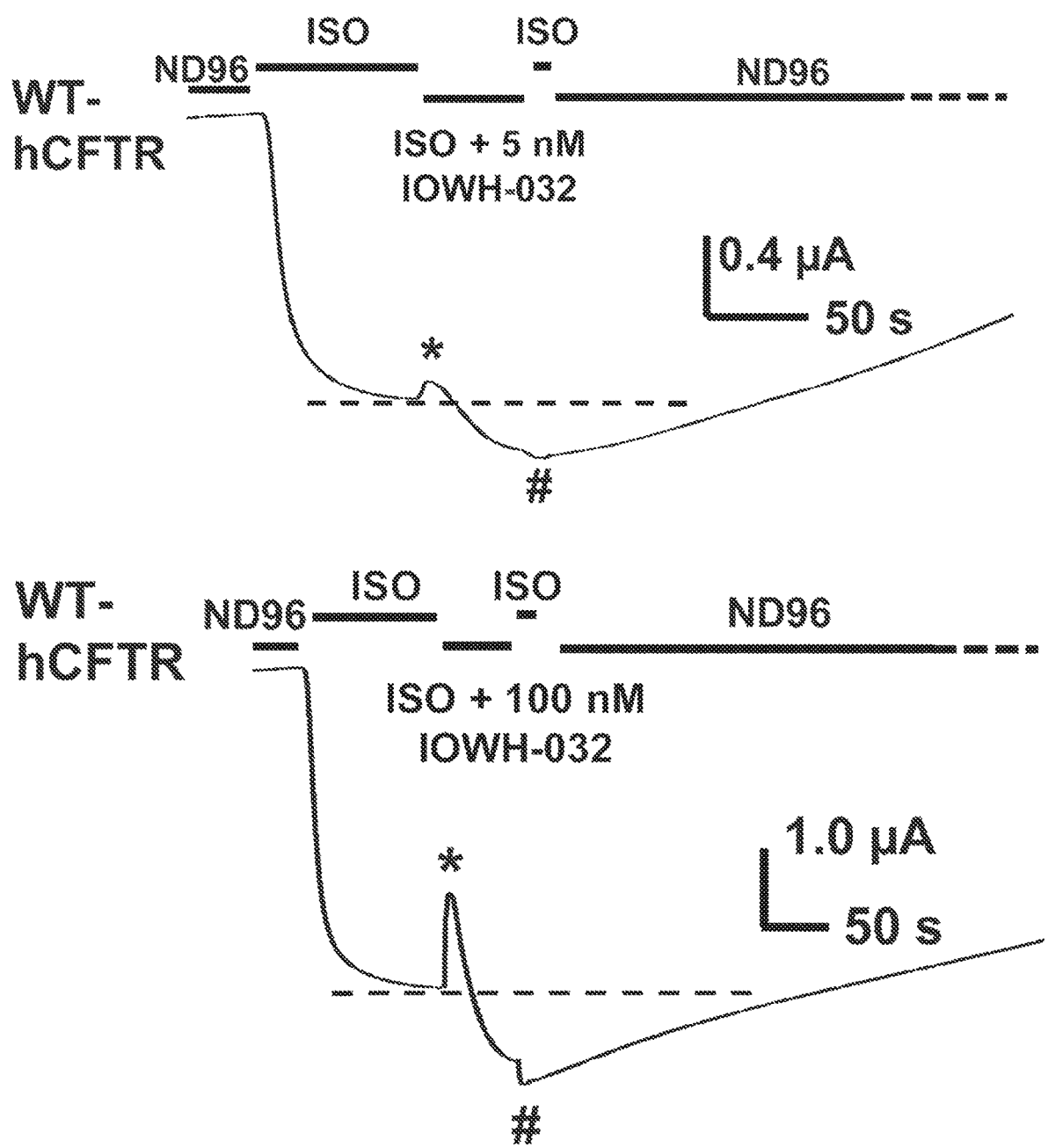
FIG. 2A shows data indicating iOWH-032 both inhibited and potentiated wildtype human CFTR (WT-hCFTR) (Kds=6.1 and 0.64 nM, respectively).
Figure 2B:
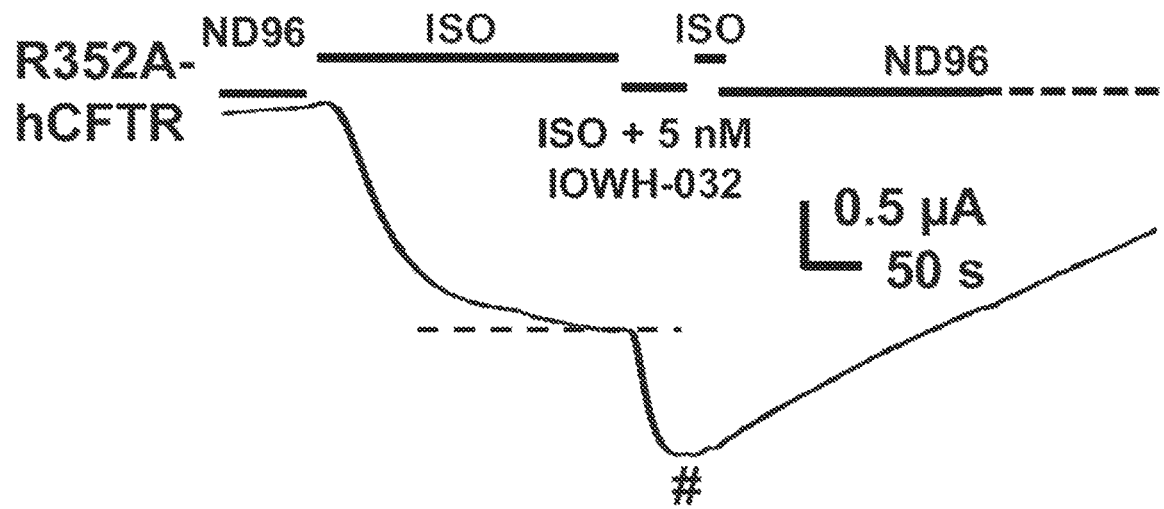
FIG. 2B shows data indicating iOWH-032 potentiated but did not inhibit for human CFTR with a R352A mutation.
Figure 2C:
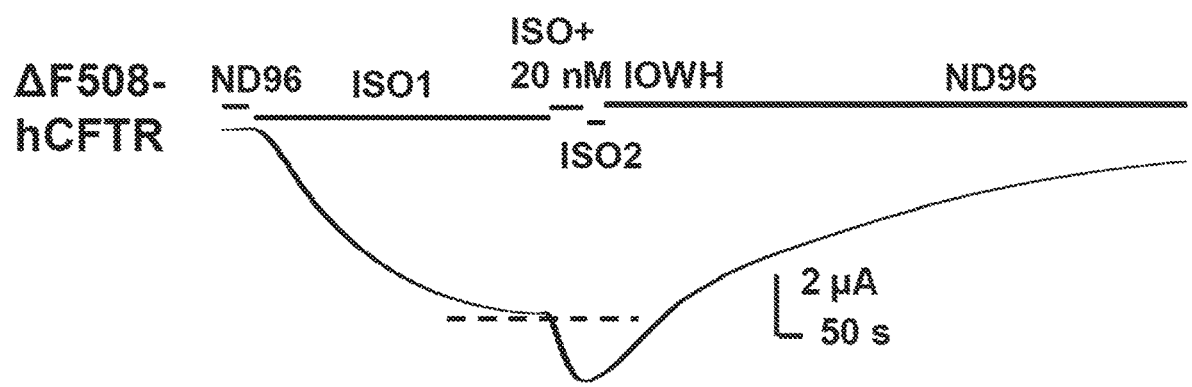
FIG. 2C shows data indicating iOWH-032 potentiated but did not inhibit for human CFTR with an F508 del mutation.
Figure 3A:
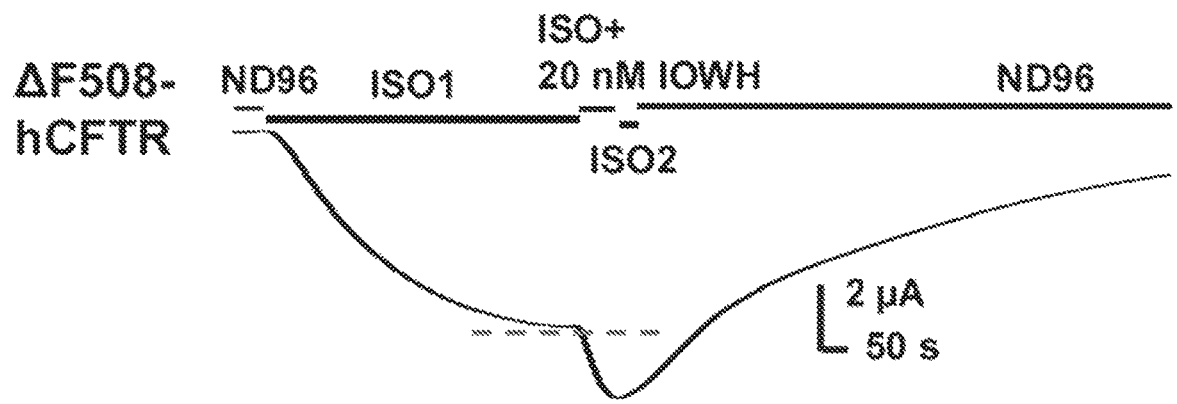
FIG. 3A shows data on iOWH for F508-del mutation in hCFTR.
Figure 3B:
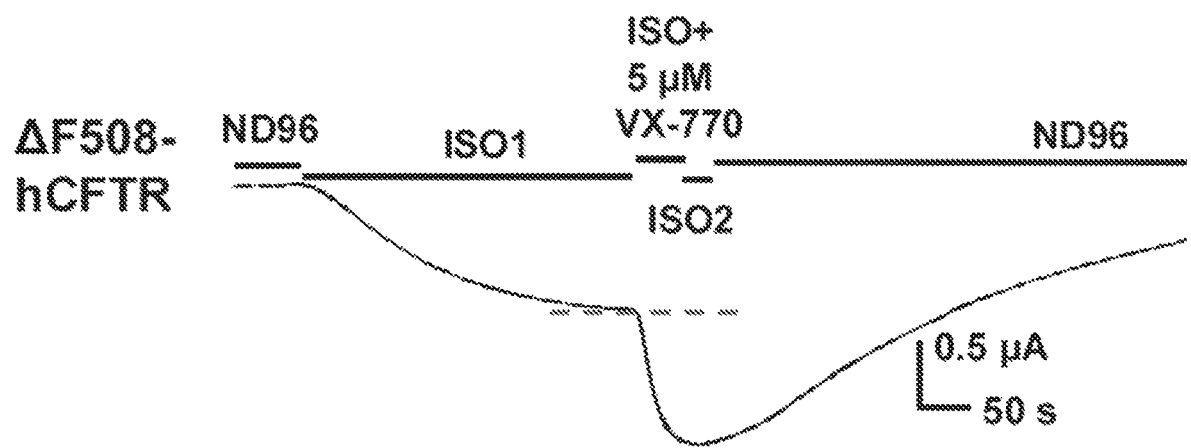
FIG. 3B shows data on ivacaftor (VX-770) for F508-del mutation in hCFTR.

Work on certain inventions in this disclosure was supported by grants from the Cystic Fibrosis Foundation.
Testing of Compounds In order to identify compounds that potentiate F508del-hCFTR expressed in *Xenopus* oocytes, the effects of IOWH-032 on WT, R352A, and F508del-hCFTR were studied using the two-electrode voltage clamp (TEVC) technique. Oocytes do not exhibit the impaired trafficking of F508del-hCFTR to the plasma membrane. See Drumm et al. Chloride conductance expressed by delta F508 and other mutant CFTRs in *Xenopus* oocytes. Science, 1991, 254(5039): 1797-1799. Representative current traces and summary data are shown in FIGS. 2A-C. Extracellular exposure to IOWH-032 potentiated WT and F508del-hCFTR channels.

Preparation of Oocytes and cRNA and Electrophysiology

Human CFTR cRNAs used in electrophysiology experiments were prepared from constructs encoding WT-hCFTR in the pGEMHE vector (hCFTR/pGEMHE kindly provided by Dr. D. Gadsby, Rockefeller University). The mutants of hCFTR used in this study were prepared using site-directed mutagenesis with the Quikchange protocol (Stratagene, La Jolla, Calif.) and mutant constructs were verified by sequencing across the entire open reading frame before use. *Xenopus laevis* oocytes were injected with 0.4-10 ng of CFTR cRNAs, and were incubated at 17° C. in modified Liebovitz's L-15 media with the addition of HEPES (pH 7.5), penicillin, and streptomycin. Recordings were made typically 24-96 hours after the injection of cRNAs.

For inside-out macropatch recording, pipettes were pulled from borosilicate glass (Sutter Instrument Co., Novato, Calif.) and pipette resistances were 1-2 MΩ when filled with chloride-containing pipette solution (in mM): 150 NMDG-Cl, 5 $MgCl_2$, 10 TES (pH 7.5). Channels were activated by excision into cytoplasmic solution containing (in mM): 150 NMDG-Cl, 1.1 $MgCl_2$, 2 Tris-EGTA, 10 TES, 1 MgATP (Adenosine 5'-triphosphate magnesium), and different concentrations of PKA (pH 7.5). CFTR channels were studied in excised, inside-out patches at room temperature (22-23° C.). Oocytes were prepared for study by shrinking in hypertonic solution followed by manual removal of the vitelline membrane. Macropatch recordings were performed with an Axopatch 200B amplifier operated by pClamp 8.2 software; data were filtered at 100 Hz with a four-pole Bessel filter and acquired at 2 kHz. The voltage protocol used in this project was applied every 5 s: hold at Vm=0 mV, then step to +100 mV for 50 ms followed by a ramp down to −100 mV over 300 ms prior to return to 0 mV.

Standard two-electrode voltage clamp (TEVC) techniques were used to study the effects of chemicals with application of reagents to the extracellular bath. Each oocyte was injected with CFTR cRNA along with cRNA encoding the beta2-adrenergic receptor (P2AR). Electrode resistances measured 0.5-1.4 MS when filled with 3 M KCl and measured in standard ND96 bath solution that contained (in mM): 96 NaCl, 2 KCl, 1 MgCl2, and 5 HEPES (pH 7.5). CFTR channels were activated by exposure to 10 μM isoproterenol (ISO) in ND 96 and alternatively assayed in the presence or absence of different concentrations of compounds in the bath solution, typically in the continuing presence of ISO. Currents were acquired with an Axoclamp 900A amplifier and Clampex 10.2 software, and current data were digitized at 2 kHz.

---

The invention claimed is:

1. A pharmaceutical composition comprising 3-(3,5-dibromo-4-hydroxyphenyl)-N-(4-phenoxybenzyl)-1,2,4-oxadiazole-5-carboxamide, or salt thereof, lumacaftor, and a pharmaceutically acceptable excipient.

2. The pharmaceutical composition of claim 1, in the form of a pill, tablet, or capsule.

3. The pharmaceutical composition of claim 1, in the form of an aqueous buffer solution.

4. The pharmaceutical composition of claim 1, wherein the pharmaceutically acceptable excipient is a saccharide or polysaccharide.

5. The pharmaceutical composition of claim 1, wherein the pharmaceutically acceptable excipient is lactose, sucrose, mannitol, triethyl citrate, or dextrose.

6. The pharmaceutical composition of claim 1, wherein the pharmaceutically acceptable excipient is cellulose, methyl cellulose, ethyl cellulose, hydroxyl propyl cellulose, hydroxypropyl methylcellulose, carboxymethylcellulose, or salt thereof.

7. The pharmaceutical composition of claim 1, wherein the pharmaceutically acceptable excipient is povidone or crospovidone.

8. The pharmaceutical composition of claim 1, wherein the pharmaceutically acceptable excipient is a methyl and ethyl acrylate copolymer.

9. The pharmaceutical composition of claim 1, wherein the pharmaceutically acceptable excipient is polyethylene glycol.

10. The pharmaceutical composition of claim 1, wherein the pharmaceutically acceptable excipient is a fatty acid ester of sorbitol, sorbic acid or salt thereof.

11. The pharmaceutical composition of claim 1, wherein the pharmaceutically acceptable excipient is lauryl sulfate or salt thereof.

12. The pharmaceutical composition of claim 1, wherein the pharmaceutically acceptable excipient is gelatin.

13. The pharmaceutical composition of claim 1, wherein the pharmaceutically acceptable excipient is glycerin, glyceryl monooleate, or triacetin.

14. The pharmaceutical composition of claim 1, wherein the pharmaceutically acceptable excipient is silicon dioxide or titanium dioxide.

15. The pharmaceutical composition of claim 1, wherein the pharmaceutically acceptable excipient is stearic acid, magnesium stearate, or calcium stearate.

16. The pharmaceutical composition of claim 1, wherein the pharmaceutically acceptable excipient is calcium phosphate.

17. The pharmaceutical composition of claim 1, wherein the pharmaceutically acceptable excipient is starch or carboxymethyl ethers of starch.

18. The pharmaceutical composition of claim 1, wherein the pharmaceutically acceptable excipient is iron oxide.

19. The pharmaceutical composition of claim 1, wherein the pharmaceutically acceptable excipient is castor oil or mineral oil.

20. The pharmaceutical composition of claim 1, wherein the pharmaceutically acceptable excipient is carnauba wax.

* * * * *